US010473623B2

(12) United States Patent
Ahmad et al.

(10) Patent No.: US 10,473,623 B2
(45) Date of Patent: Nov. 12, 2019

(54) SLUG FLOW MONITORING AND GAS MEASUREMENT

(71) Applicant: Saudi Arabian Oil Company, Dhahran (SA)

(72) Inventors: Talha Jamal Ahmad, Dhahran (SA); Michael J. Black, Dhahran (SA); Mohamed N. Noui-Mehidi, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 15/697,681

(22) Filed: Sep. 7, 2017

(65) Prior Publication Data
US 2017/0363580 A1 Dec. 21, 2017

Related U.S. Application Data

(63) Continuation of application No. 14/626,265, filed on Feb. 19, 2015, now Pat. No. 9,778,226.

(51) Int. Cl.
G01N 29/02 (2006.01)
E21B 43/12 (2006.01)
E21B 47/10 (2012.01)
G01F 1/66 (2006.01)
G01F 1/74 (2006.01)

(52) U.S. Cl.
CPC ............ *G01N 29/02* (2013.01); *E21B 43/12* (2013.01); *E21B 47/101* (2013.01); *G01F 1/66* (2013.01); *G01F 1/667* (2013.01); *G01F 1/74* (2013.01); *G01N 2291/02433* (2013.01)

(58) Field of Classification Search
None
See application file for complete search history.

(56) References Cited

U.S. PATENT DOCUMENTS 4,080,837 A 3/1978 Alexander et al.
4,381,674 A 5/1983 Abts
(Continued)

FOREIGN PATENT DOCUMENTS

CN 202916242 5/2013
CN 103733061 4/2014
CN 104155358 11/2014

OTHER PUBLICATIONS

Communication Pursuant to Article 94(3) EPC issued in European Application No. 15794772.2 dated Jul. 23, 2018, 6 pages.
(Continued)

*Primary Examiner* — Daniel S Larkin
(74) *Attorney, Agent, or Firm* — Fish & Richardson P.C.

(57) ABSTRACT

Methods, systems, and apparatus, including computer programs encoded on a computer storage medium, for monitoring slug flow in subterranean wells. In one aspect, a method includes at a time instant, transmitting an acoustic signal across a cross-section of a pipeline flowing multiphase fluid including gaseous fluid and liquid fluid, wherein a portion of the acoustic signal is carried through the cross-section of the pipeline by the multiphase fluid and determining, at the time instant, a first quantity of the gaseous fluid and a second quantity of the liquid fluid passing the cross-section of the pipeline based, in part, on an energy of the portion of the acoustic signal carried through the cross-section and at least a portion of a total energy of the transmitted acoustic signal.

11 Claims, 5 Drawing Sheets

(56) References Cited

U.S. PATENT DOCUMENTS

| | | | |
|---|---|---|---|
| 4,527,420 | A | 7/1985 | Foote |
| 5,115,670 | A | 5/1992 | Shen |
| 5,148,405 | A | 9/1992 | Belchamber et al. |
| 5,415,048 | A | 5/1995 | Diatschenko et al. |
| 5,561,245 | A | 10/1996 | Georgi et al. |
| 5,714,691 | A | 2/1998 | Hill |
| 6,151,958 | A | 11/2000 | Letton et al. |
| 7,036,356 | B2 | 5/2006 | Leppanen et al. |
| 7,562,584 | B2 | 7/2009 | Conquergood |
| 7,775,125 | B2 | 8/2010 | Rhodes |
| 8,061,186 | B2 | 11/2011 | Gysling |
| 2008/0163700 | A1 | 7/2008 | Huang |

OTHER PUBLICATIONS

Gulf Cooperation Council Examination Report issued in GCC Application No. GC 2016/30883 dated May 23, 2018, 4 pages.

Gulf Cooperation Council Examination Report issued in GCC Application No. 2016-30883 dated Nov. 8, 2018, 3 pages.

Chinese Office Action issued in Chinese Application No. 201580076590.9 dated Apr. 19, 2019, 19 pages.

Addali et al., "Acoustic Emission and Gas-Phase Measurements in Two-Phase Flow," published in 2010, 11 pages.

Alssayh et al., "Determining Slug Velocity in Two-Phase Flow with Acoustic Emission," Sep. 2012, 8 pages.

Dos Reis et al., "A Non-Intrusive Probe for Bubble Profile and Velocity Measurement in Horizontal Slug Flows," Science Direct, Published in 2005, pp. 229-239.

Hanyang et al., "Experimental Investigation of Slug Development on Horizontal Two-Phase Flow," Chinese Journal of Chemical Engineering, 16(2), Copyright, 2008, pp. 171-177.

Shuib Husin et al., "Acoustic Emission for Monitoring Two-Phase Flow," EWGAE 2010, Sep. 2010, 7 pages.

Zhang et al., "A Measurement Method of Slug Flow Velocity of Gas-Liquid Two-Phase Flow in Horizontal Pipe," Copyright 2010, 5 pages.

Nydal et al., "Statistical Characterization of Slug Flow in Horizontal Pipes", Int. J. Multiphase Flow, vol. 18, No. 3, Published in 1992, pp. 439-453.

Sanderson, M.L. et al.; "Guidelines for the Use of Ultrasonic Non-Invasive Metering Techniques"; Flow Measurement and Instrumentation; vol. 13, No. 4; Aug. 31, 2002; pp. 125-142.

International Search Report and Written Opinion of the International Searching Authority issued in International Application No. PCT/US2015/059159 dated Apr. 5, 2016; 14 pages.

Communication under Rule 71(3) EPC issued in European Application No. 15794772.2 dated Dec. 6, 2018, 34 pages.

Chinese Office Action issued in Chinese Application No. 201580076590.9 dated Oct. 25, 2018, 18 pages.

"Constructing Experiment Platform of Ultrasonic Attenuation Concentration Meter", Nov. 2007, 3 pages English Abstract.

SLUG FLOW MONITORING AND GAS MEASUREMENT

This application is a continuation of and claims priority to U.S. application Ser. No. 14/626,265 (issued as U.S. Pat. No. 9,778,226) entitled "Slug Flow Monitoring and Gas Measurement" filed on Feb. 19, 2015, the entire contents of which are incorporated herein by reference in its entirety.

TECHNICAL FIELD

This specification relates to flow in subterranean zones from which hydrocarbons can be recovered.

BACKGROUND

Hydrocarbons, such as oil and gas, can be retrieved from subterranean zones using a well or a wellbore drilled into the subterranean formation. In some cases, the wellbore is lined by casing, which typically is a hollow steel pipe that is perforated by each production zone to extract fluids from the subterranean formation. Fluid from each production zone entering the wellbore is drawn into the tubing and guided towards the surface. For example, the fluid moves from the reservoir to the annular space, from where it can flow to an inflow control device and finally to the base pipe. The geometry of the wellbore, such as uneven drainage, can lead to a multiphase flow, due to the invasion of a gas cone or a water cone. It is common in hydrocarbon well operations to have two or more types of fluids flowing through a downhole tubular positioned in a wellbore extending through the subterranean zone. For example, during production, the fluids in the wellbore tend to separate into zones of oil, water, gas and solid (e.g., sand) flow.

SUMMARY

This specification describes technologies relating to monitoring slug flow in subterranean wells and measuring gas quantities in the slug flow.

Some aspects of the subject matter described here can be implemented as a method including at a time instant, the transmission of an acoustic signal across a cross-section of a pipeline flowing multiphase fluid including gaseous fluid and liquid fluid and determining, at the time instant, a first quantity of the gaseous fluid and a second quantity of the liquid fluid passing the cross-section of the pipeline based, in part, on an energy of the portion of the acoustic signal carried through the cross-section and at least a portion of a total energy of the transmitted acoustic signal. A portion of the acoustic signal is carried through the cross-section of the pipeline by the multiphase fluid.

This, and other aspects, can include one or more of the following features. At each subsequent time instant of a plurality of subsequent time instants a subsequent acoustic signal is transmitted across the cross-section of the pipeline. A portion of the subsequent acoustic signal is carried through the cross-section of the pipeline by the multiphase fluid. A third quantity of the gaseous fluid and a fourth quantity of the liquid fluid passing the cross-section of the pipeline is determined based, in part, on an energy of the portion of the subsequent acoustic signal carried through the cross-section and an energy of the transmitted subsequent acoustic signal. A composition of the multiphase fluid flowed through the cross-section during the time instant and the plurality of subsequent time instants is determined. The transmission of the acoustic signal across the cross-section of the pipeline includes attaching an acoustic signal transmitter to a first location on the cross-section of the pipeline and connecting an acoustic signal generator to the acoustic signal transmitter, the acoustic signal generator to generate the acoustic signal. The acoustic signal transmitter is attached to transmit the acoustic signal at a beam angle ranging between about 5° and 15°. The acoustic signal transmitter is configured to generate an acoustic signal in a frequency range of between about 0.5 MHz and 2.0 MHz. The acoustic signal generator is configured to generate and transmit an electric signal to the acoustic signal transmitter, and the acoustic signal transmitter is configured to convert the electric signal into the acoustic signal. An acoustic signal receiver is attached to a second location on the cross-section of the pipeline and an acoustic signal evaluator is connected to the acoustic signal receiver. The acoustic signal transmitter and the acoustic signal receiver are attached at diametrically opposite ends of the cross-section of the pipeline. The acoustic signal includes an amplitude determined based on a deviation in pressure from a mean ambient pressure. A first quantity of the gaseous fluid and a second quantity of the liquid fluid passing the cross-section of the pipeline are determined at the time instant based, in part, on an energy of the portion of the acoustic signal carried through the cross-section and an energy of the transmitted acoustic signal includes determining an energy of the portion of the acoustic signal carried through the cross-section.

$$E_S = \Sigma_{n=1}^{N} |x_n|^2 \Delta t$$

In some embodiments, the quantity of the gaseous fluid and the quantity of the liquid fluid passing the cross-section of the pipeline are determined, at the time instant, based, in part, on an energy of the portion of the acoustic signal carried through the cross-section. An energy of the transmitted acoustic signal includes determining that the energy of the portion of the acoustic signal carried through the cross-section and the energy of the transmitted acoustic signal are substantially equal and determining that multiphase fluid includes more liquid fluid than gaseous fluid. In some embodiments, the quantity of the gaseous fluid and a quantity of the liquid fluid passing the cross-section of the pipeline are determined, at the time instant, based, in part, on an energy of the portion of the acoustic signal carried through the cross-section. An energy of the transmitted acoustic signal includes: determining that the energy of the portion of the acoustic signal carried through the cross-section is substantially less than the energy of the transmitted acoustic signal and determining that multiphase fluid includes substantially more gaseous fluid than liquid fluid.

Some aspects of the subject matter described here can be implemented as a system to analyze multiphase fluid in a pipeline. The system includes an acoustic transmitter to attach to a first location of the pipeline flowing multiphase fluid including gaseous fluid and liquid fluid, the acoustic transmitter to transmit an acoustic signal of a first energy across a cross-section of a pipeline flowing multiphase fluid including gaseous fluid and liquid fluid. The system also includes an acoustic receiver to attach to a second location of the pipeline, the acoustic receiver to receive a portion of the acoustic signal carried by the multiphase fluid across the pipeline, the portion of the acoustic signal having a second energy and an acoustic signal evaluator to determine a quantity of the gaseous fluid and a quantity of the liquid fluid passing the cross-section of the pipeline based, in part, on the second energy and the first energy.

This, and other aspects, can include one or more of the following features. The system includes an acoustic signal generator to generate the acoustic signal. The acoustic signal generator is connected to the acoustic transmitter, wherein the acoustic signal generator is configured to generate and transmit an electric signal to the acoustic signal transmitter, and wherein the acoustic signal transmitter is configured to convert the electric signal into the acoustic signal.

$$E_S = \sum_{n=1}^{N} |x_n|^2 \Delta t$$

In some embodiments, the acoustic signal transmitter is attached to the first location to transmit the acoustic signal at a beam angle ranging between about 5° and 15°. The acoustic signal transmitter is configured to generate an acoustic signal in a frequency range of between about 0.5 MHz and 2.0 MHz.

Some aspects of the subject matter described here can be implemented as a method including transmitting an acoustic signal across a cross-section of a pipeline flowing multiphase fluid including gaseous fluid and liquid fluid, receiving the acoustic signal carried by the multiphase fluid through the cross-section of the pipeline, determining an energy level of the received acoustic signal and determining flow parameters of the multiphase fluid based, in part, on the determined energy level of the received acoustic signal.

This, and other aspects, can include one or more of the following features. The transmission of the acoustic signal across the cross-section of the pipeline includes the acoustic signal through an acoustic transmitter attached to an outer surface of the pipeline at a first location, wherein receiving the acoustic signal carried by the multiphase fluid through the cross-section of the pipeline includes receiving the acoustic signal carried by the multiphase fluid at an acoustic receiver attached to an outer surface of the pipeline at a second location, and wherein the first location and the second location are diametrically opposite on the cross-section. The flow parameters include at least one of a slug velocity, a slug frequency and a slug length. The slug velocity is determined based on correlating the acoustic signal received at two locations of the pipeline and a travel time between the two locations.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1A:
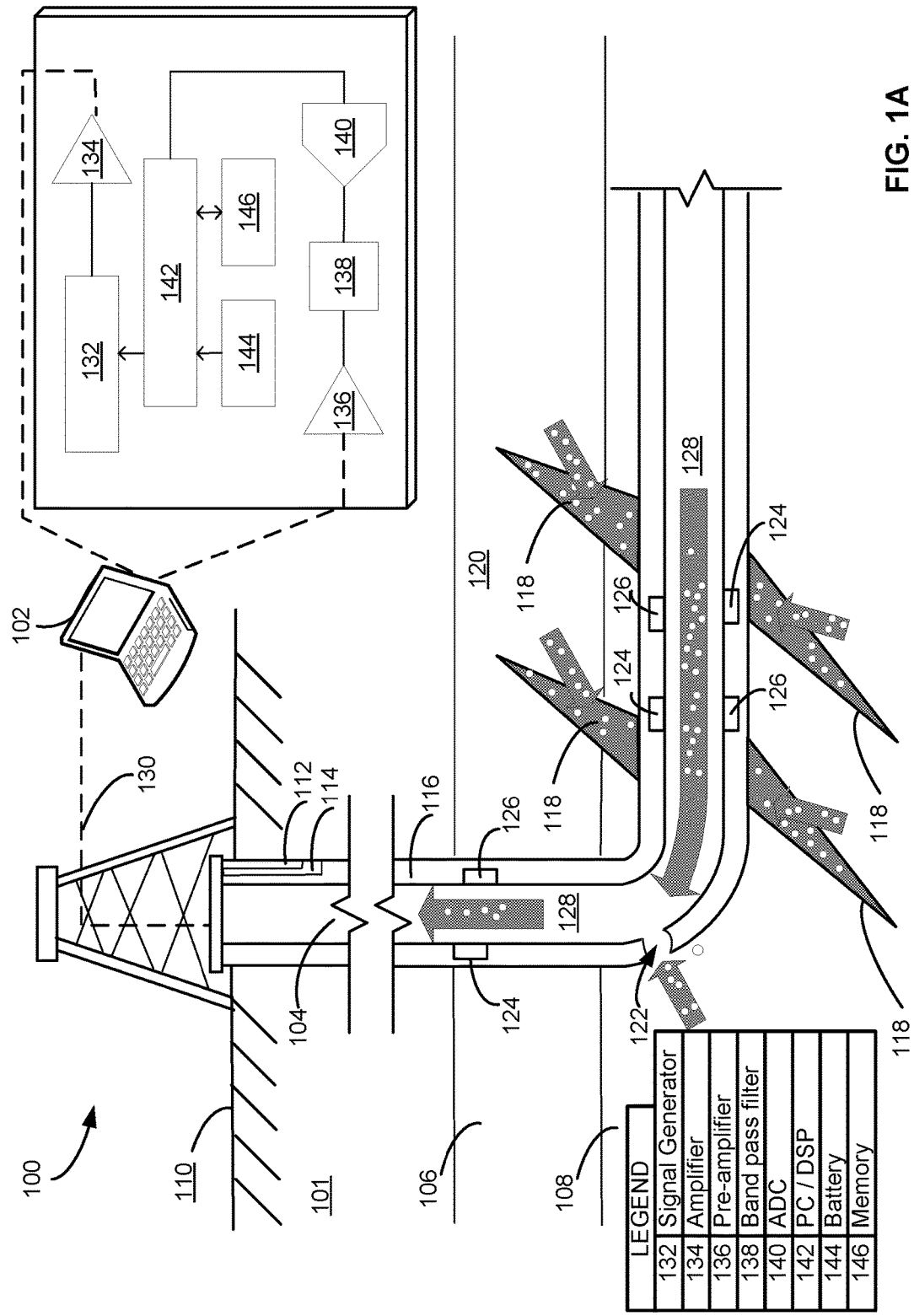
FIG. 1A illustrates an example well system for monitoring slug flow.

This specification relates to monitoring flow in subterranean wells. The fluid flowing through subterranean wells can include oil, water, gas and solid (e.g., sand). The coexistence of different types of fluids generates a multiphase flow that implies that fluid composition may vary from point to point within the wellbore as a function of pressure, temperature and slip between the phases. The multiphase flow can depend on a number of factors including the relative density ratio of one fluid to the other, difference in viscosity between fluids, and velocity (e.g., slip) of each fluid. The multiphase flow in subterranean wells can vary during the production life of a well or a group of wells whose flow is commingled in a common production line. For example, the production of gas can increase during the life of an oil-bearing formation, particularly if gas is being used as a drive fluid to force crude oil to the production well or wells. In such cases the gas concentration increases and concentrations of other fluid components decreases.

The multiphase flow often results in so-called slug flow, in which slugs of liquid occur in the flow lines that are connected to the separation, treatment and pumping equipment. The slug flow regime can be encountered frequently for a wide range of oil and gas flow rates. Slug flow in liquid-gas compositions can affect the flow line designs and the mechanical integrity of the oil production system. Consequently, monitoring slug flow in liquid-gas compositions can be useful.

Implementations of the subject matter described in this specification are generally directed to multiphase flow monitoring in subterranean wells. Some implementations include an automatic computation of a set of properties of a slug flow in subterranean wells. Slug flow is a multiphase flow that can start with two different phases, in which the gas phase, for instance, exists as large bubbles separated by liquid slugs. In some examples, each gas pocket is followed by a train of bubbles in the liquid phase that define the slug tail. Slug flow can be generated inside the wellbore and continue in pipelines, to the surface processing facilities. Knowledge of slug flow parameters including the frequency, velocity and length of the slugs can improve the efficient design and operation of pipelines.

Particular embodiments of the subject matter described in this specification can be implemented so as to realize one or more of the following advantages. The accuracy and reliability of the proposed method to monitor the multiphase flow is independent from the amount of gas void fraction. The method accounts for acoustic variability and non-stationary nature of the signal. Any of the described methods can be coupled with arrays of sensors so that precursor conditions to slugging could be detected and the slugging itself could be prevented. The disclosed system engineered as a slug low metering solution can be installed either in surface applications as top sides off-shore or on-shore locations and it can also be deployed downhole as part of a permanent or retrievable system. The system characteristics allow for compact packaging of the metering system and can efficiently function at low power. The method was designed to be computationally inexpensive and the system can be developed at a low cost.

As shown in FIG. 1A, an example well system 100 can be implemented during well production to monitor slug flow in a subterranean formation 101. Measurement of slug flow can support the optimization of well production. The example well system 100 includes a wellbore 104 formed with a drilling assembly (not shown). The drilling assembly can be used to form a vertical wellbore portion extending from the terranean surface 110 and through one or more subterranean formations 106 and/or 108 (or other subterranean formations or zones). The subterranean region can include a reservoir 120 that contains hydrocarbon resources, such as oil, natural gas, and/or other hydrocarbon resources. The reservoir 120 can include porous and permeable rock containing liquid and/or gaseous hydrocarbons, such as oil, water or other liquids. The reservoir 120 can include a conventional reservoir, a non-conventional reservoir, a tight gas reservoir, and/or other types of reservoir. The well system 100 produces the resident hydrocarbon resources from the reservoir 120 to the surface 110 through the wellbore 104.

The wellbore 104 in the well system 100 can include any combination of horizontal, vertical, slant, curved, articulated, lateral, multi-lateral and/or other well bore geometries that can affect the fluid flow through the wellbore. One or more wellbore casings, such as a conductor casing 112, an intermediate casing 114, and a production casing 116 can be installed in at least a portion of the vertical portion of the wellbore 104 and/or other wellbore portion. Alternatively, in some embodiments, one or more of the casings 112, 114, and 116 cannot be installed (e.g., an open hole completion).

In some embodiments, the wellbore 104 can include multiple discontinuities (e.g. perforations, fractures, or other discontinuities). FIG. 1A illustrates exemplary discontinuities 122 and fractures 118. The discontinuities 122 can include a communication tunnel created from the casing 116 into the reservoir formation 120, through which oil or gas is produced. The geometry of the perforation 122 can depend on the method used to create the perforation 122 and can affect the fluid flow through the wellbore.

In a first embodiment, system 100 includes an acoustic pair formed of a transmitter 124 and a receiver 126. The transmitter 124 and the receiver 126 can be attached to the wellbore 104 (e.g., to the production casing 116) such that the surface of the transmitter 124 and the surface of the receiver 126 are in direct contact with the fluid flow. In some implementations, a non-invasive configuration of the system (where the acoustic transmitter 124 and the receiver 126 pairs are not in direct contact with the fluid flow) can be used. In the non-invasive configuration of the system, the acoustic transmitter 124 and the receiver 126 pairs can be clamped on the pipeline using a couplant between the surface of the transmitter 124 and the wellbore 104 as well as using a couplant between the surface of the receiver 126 and the wellbore 104, thus forming a removable system that does not affect the structure of the wellbore 104.

Figure 1B:
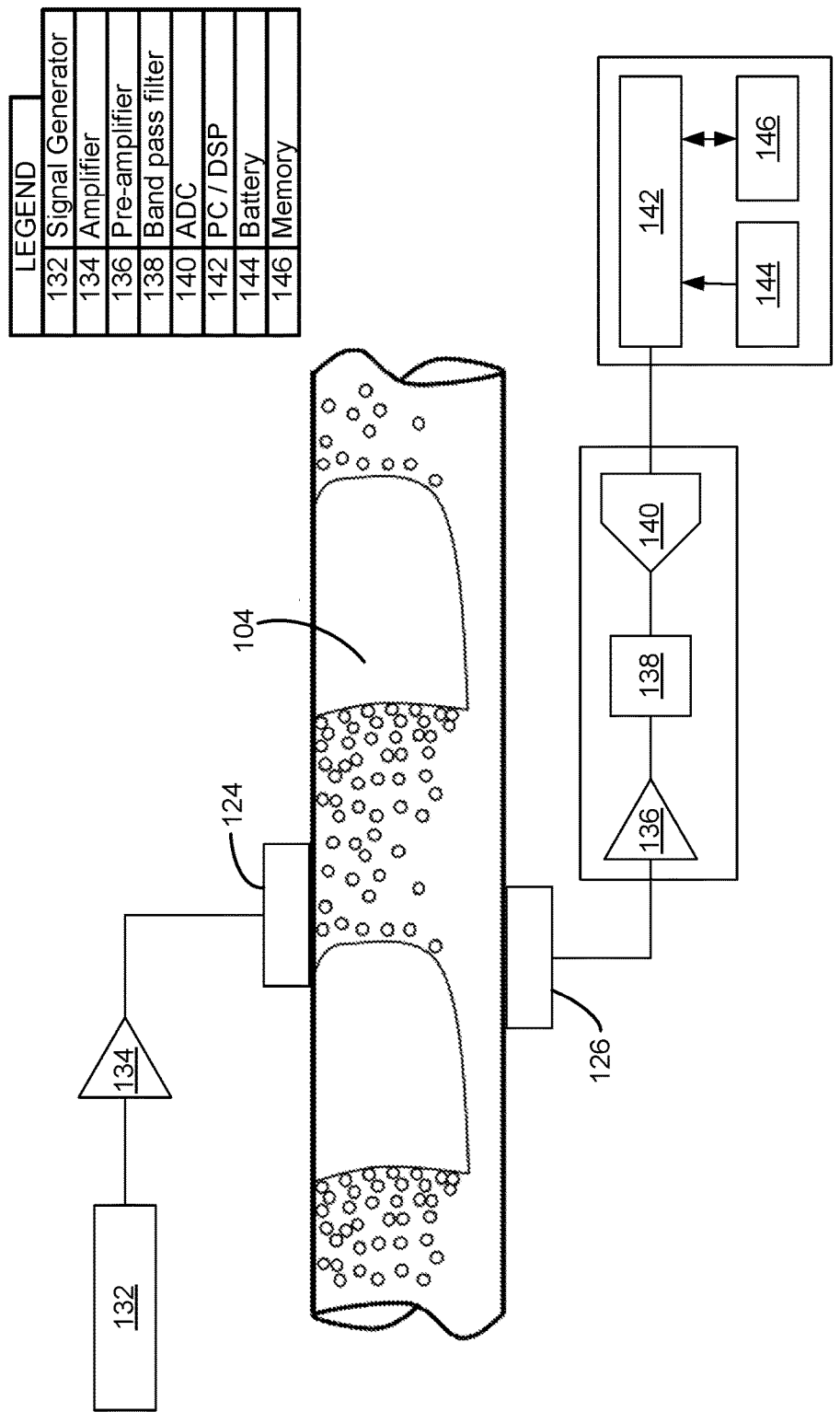
FIG. 1B illustrates another example well system for monitoring slug flow.
Figure 1C:
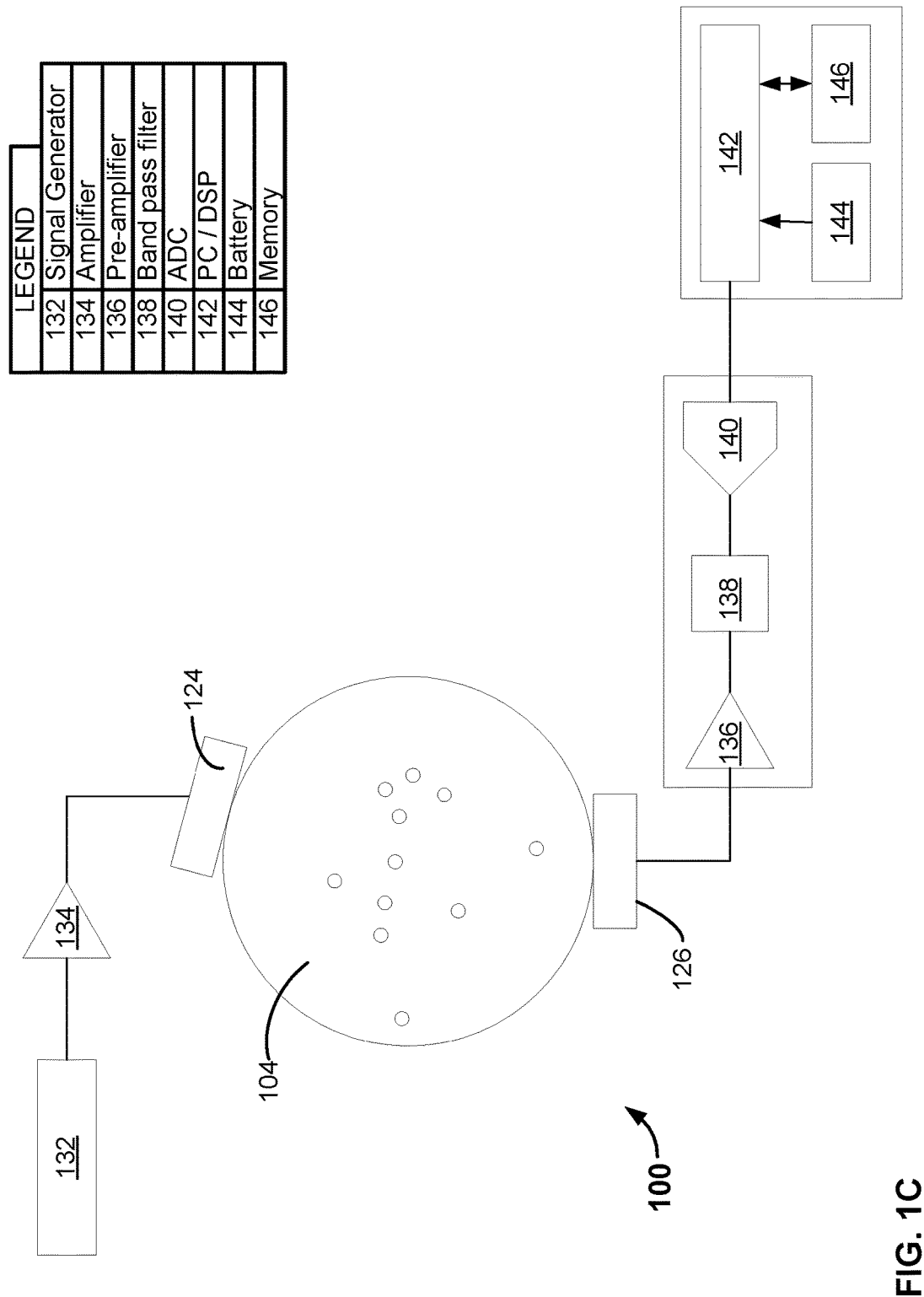
FIG. 1C illustrates a cross-sectional view of an example well system for monitoring slug flow.

In some implementations, as illustrated in FIG. 1A, the transmitter 124 and the receiver 126 can be attached to diametrically opposite ends of the cross-section of the pipeline. In some implementations, as illustrated in FIGS. 1A, 1B and 1C, the transmitter 124 and the receiver 126 are offset from a cross-section taken perpendicular to a longitudinal axis of the wellbore 104. The transmitter 124-receiver 126 pair can be operated to monitor multiphase flow at one time instant or at multiple time instants.

In another embodiment, as illustrated in FIG. 1A, system 100 includes a plurality of acoustic pairs formed of multiple transmitters 124 and a corresponding number of receivers 126. Each acoustic pair has the same characteristics as the transmitter 124-receiver 126 pair in the first embodiment. Each transmitter 124 receiver 126 pair can be attached to the wellbore 104 at different depths, positions and/or orientations, and can monitor multiphase flow at one or more time instants. The first embodiment allows determining a multiphase flow profile across a cross-section of the pipeline, while the second embodiment allows determining a flow profile across the length of the pipeline.

In some implementations, the transmitter 124 and the receiver 126 can be positioned on a wellhead to monitor slug flow from a well. The transmitter 124 and the receiver 126 can also be deployed downhole, inside a well for slug flow monitoring from wellbore. The transmitter 124 and the receiver 126 can be a part of a permanent smart completion, or a retrievable system in motherbore or laterals. The transmitter 124 and the receiver 126 can be positioned at an arbitrary angle relative to each other (for example in this range: 5°-15°). In an extreme case certain multiphase flows, such as bubbly flow, can produce a strong reflection signal, raising difficulties in co-locating the transmitter 124 and the receiver 126 or even use a single transceiver 124 and 126. Coverage of the full range of multiphase flows can require multiple angles of interrogation. Modifying the angular response in particular situations can result in a more accurate measurement of the flow regime.

The transmitter 124 and receiver 126 can operate at a fixed high frequency (e.g., in the range: 0.5-2 MHz) with a narrow beam angle (in this range: 5°-15°). Among different transmitter 124/receiver 126 pairs, one pair can operate at the same or different frequencies than another transmitter 124 and receiver 126 pair. The transmitter 124 can transmit an acoustic signal being driven by an electric signal generated by a signal generator 132 and amplified by an amplifier 134. The signal generator (e.g., oscillator) 132 can generate a continuous sinusoidal wave signal of high frequency (e.g., 0.5-2 MHz) and low voltage (e.g., 5-10V) characterized by a particular amplitude, frequency and phase. In some implementations, more complex waveforms can be generated where, for example, the frequency of the input signal can be chirped from a low frequency to a high frequency over a fixed period of time which can be used to cover the frequency space.

A chirp or a sweep signal can be used in which the frequency is swept linearly or exponentially from a low frequency (as low as 100 KHz) to a high frequency (2 MHz) in a fixed period of time. Such a signal can provide valuable information about acoustic signal transmission through the flow over the full frequency spectrum. The chirp or a sweep signal can help in improving the accuracy of measurement. A complex processing method can be required to extract information from a transmitted sweep signal. A lower frequency modulation of the signal in kHz or lower frequency range can be introduced in the electric signal and lock-in amplifier style measurements can be implemented to filter out noise in the measurement. The electric signal can be amplified by the amplifier 134 (e.g., a high-voltage operational amplifier) to 50-100V. The amplified electric signal is provided to drive the acoustic transmitter 124. The transmitter 124 converts the electric signal to acoustic signal and generates a continuous high-frequency (e.g., 0.5-2 MHz) acoustic signal. In some implementations, the transmission signal strength is increased to compensate for the attenuation of the acoustic signal in slug flow. The transmission signal strength can be increased by increasing the gain of the amplifier using a programmable gain amplifier instead of a fixed gain amplifier 134.

Several types of transmitters 124 can be implemented. One example of a transmitter 124 can be a piezoelectric transceiver (or transmitter) of similar construction to the receiver in which a voltage signal is used to modulate the sound waves by causing the piezoelectric stack to expand and contract as the electric field is applied across it. A piezoelectric transceiver can be tuned to a narrow range of frequencies. Another example of a transmitter 124 can be an array of high Q piezoelectric transceivers (or transmitters) with the resonant frequencies in the range of operation which is nominally 0.5-2.0 MHz. In frequency space, a selection criteria can include that for adjacent transceivers the frequency associated with the upper −3 dB point of the lower frequency transceiver coincides with the lower −3 dB point for the higher frequency transceiver. Adjacent transceivers characterized by the selection criteria can be generate a continuous frequency acoustic signal. The transceivers are smaller than the receiver or receiver array. A single voltage signal can be inputted which is then routed through a parallel array of amplifiers which supply each of the transceivers in the array individually.

In some examples, the piezoelectric element of the transceivers (or transmitters), the actuator can be replaced by a magnetostrictive material driven by the magnetic field generated by a surrounding coil. The coil can require a current supply so that a voltage signal can be inputted and fed through a current amplifier to provide a current source. The bandwidth of the transceiver 124 can be improved by using an array of magnetostrictive transceivers. Another example of transceivers (or transmitters) 124 can include an electromechanical loudspeaker system, tuned for operation at high frequencies (taking into consideration the bandwidth). A non-standard solution can be implemented to modify the operation of the electromechanical loudspeaker system from kHz regime to MHz regime, such as through MEMS (Microelectromechanical systems) based systems with the mass of the elements reduced, being adapted to operate at the selected frequency ranges. Another example of transceivers (or transmitters) 124 include an actuation system, which converts electrical energy either in the form of voltage or current into some form of movement in the frequency range of interest (MHz range).

The acoustic signal is transmitted through the slug flow and is received by the acoustic receiver 126. The acoustic receiver 126 converts the acoustic signal into an analog electric signal. The analog electric signal can be pre-amplified by a pre-amplifier 136 (e.g., a fixed gain operational amplifier). The amplified signal is filtered using a band-pass filter 138. The cutoff frequencies of the band-pass filter depend on the operating frequency and bandwidth of acoustic transmitter 124 and receiver 126. The filtered analog signal is converted to digital signal using a high resolution analog-to-digital converter (ADC) 140. The digital signal is transmitted by the ADC 140 to a personal computer (PC) or Digital Signal Processor (DSP) 142 for being processed. The PC/DSP 142 is powered by a battery 144. The processing results can be saved in a memory 146.

As illustrated in FIG. 1A, the transmitter 124 and the receiver 126 can be communicably coupled to a computing system 102 through, for example, a wireline 130. The computing system 102 can include the signal generator 132, the amplifier 134, the pre-amplifier 136, the band-pass filter 138, the ADC 140, the DSP 142, the battery 144 and the memory 146. In some embodiments, as illustrated in FIGS. 1B and 1C, the transmitter 124 is connected to the signal generator 132 and the amplifier 134, while the receiver(s) 126 is separately connected to the electronic components that process the received acoustic signal. The receiver(s) 126 can include logging capabilities to evaluate and/or measure properties of the slug flow, including quantity and composition of the fluid flowing through the well 128. The measurements can be made downhole, stored in solid-state memory for some time and later transmitted to the computing system 102 (e.g., for storage and/or analysis). In some embodiments, the received acoustic signal can be transmitted and/or transferred real-time to a surface processing system, including the pre-amplifier 136, the band-pass filter 138, the ADC 140, the DSP 142, the battery 144 and the memory 146 (e.g., over the network 130). For example, as illustrated, such properties can be stored as flow properties in the illustrated memory 146.

The transmitter 124 includes a transducer, which converts acoustic to electrical energy. The receiver 126 includes a transducer, which converts electrical to acoustic energy. As the acoustic transducers (the transmitter 124 and the receiver 126) are in acoustic contact with the liquid, a first quantity of acoustic energy can be transmitted from the transmitter 124 to the receiver 126 through a fluid without gas that is flowing through the wellbore 104. A second quantity of acoustic energy, which is smaller than the first quantity of acoustic energy can be transmitted from the transmitter 124 to the receiver 126 through a fluid formed of a mixture of gas and liquid that is flowing through the wellbore 104. A third quantity of acoustic energy, which is smaller than the second quantity of acoustic energy can be transmitted from the transmitter 124 to the receiver 126 through a fluid formed of gas that is flowing through the wellbore 104. For example, a maximum acoustic energy passes through the fluid when no gas (e.g., air or other gas) is present within the wellbore and the medium flowing through the wellbore is completely liquid and no acoustic energy can pass through passes through a fluid substantially consisting of gas (e.g., air or other gas). Since acoustic impedance of air (~400 rayl) is very different than that of crude oil (1.3 megarayl) or water (1.48 megarayl at 20° C.), liquid-air interface acts as a reflector that scatters and reflects the incoming acoustic wave in the presence of air bubbles in liquid. Such scattering and/or reflection introduces reverberations and acoustic energy loss. For example, when an elongated bubble is passing between the acoustic transmitter 124 and the receiver 126, a significant majority of the transmitted acoustic energy is reflected by liquid/air interface and no signal can be received by the acoustic receiver 126.

Figure 2:
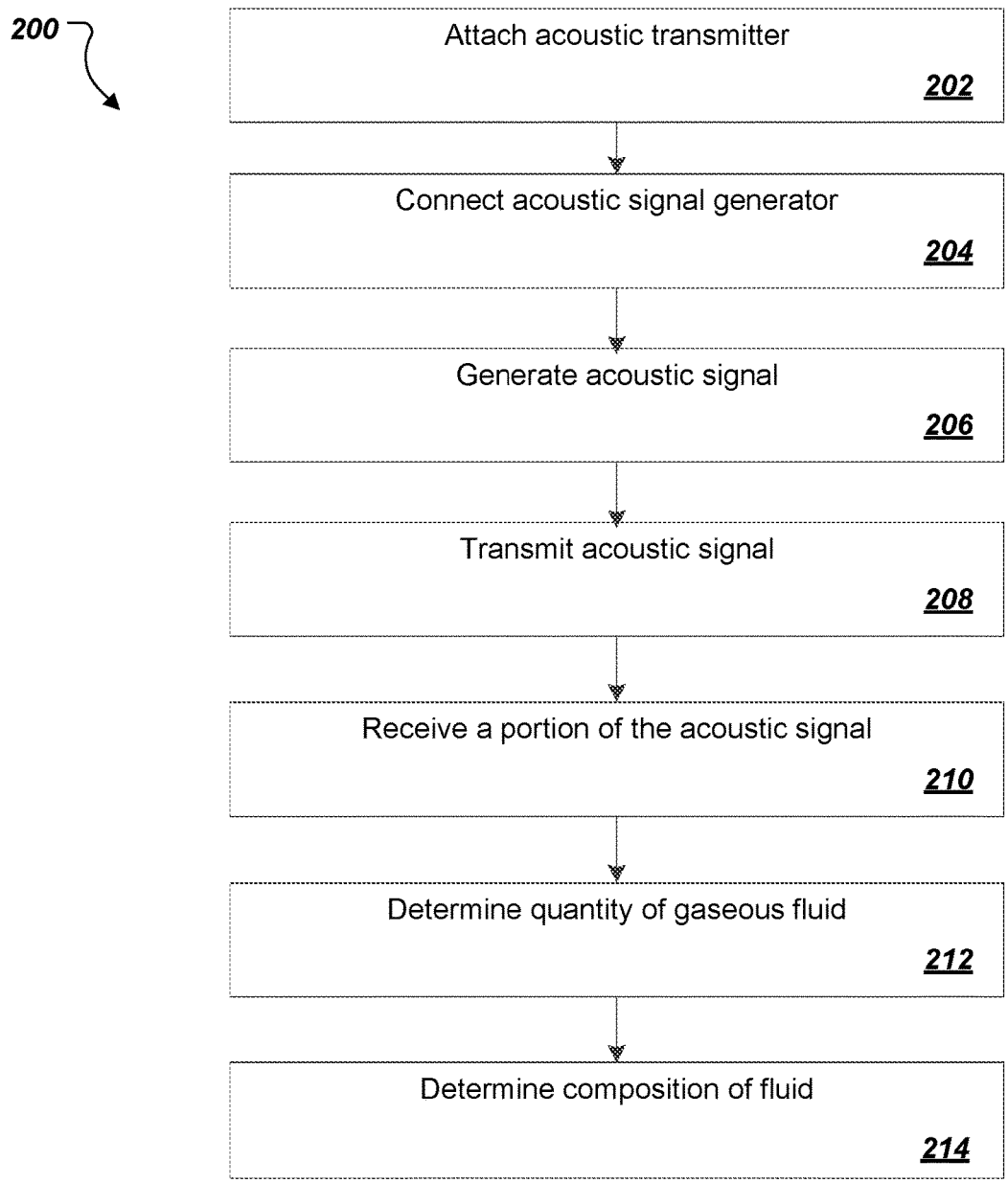
FIG. 2 is a flowchart of an example process for monitoring slug flow.

FIG. 2 is a flow chart showing an example process 200 for monitoring multiphase flow. In some instances, the process 200 is used to monitor slug flow to assist the production of fluids in a wellbore. At 202, one or more acoustic signal transmitters are attached to a first location on the cross-section of the pipeline. The acoustic signal transmitter can be placed at any location where measurement of slug flow is required. For example, the acoustic signal transmitter can be located at surface or downhole. At surface, the location can be before the downstream processing equipment (so that the operation of the processing equipment can be accordingly designed). At 204, the acoustic signal transmitter is connected to a signal generator. At 206, an acoustic signal can be generated. For example, the acoustic signal can be generated by an acoustic transmitter (e.g., transmitter 124 in FIGS. 1A-1C). At 208, the acoustic signal can be transmitted at a time instant or at multiple time instants across a cross-section of a pipeline, though which a multiphase fluid is flowing. The multiphase fluid can include gaseous fluid and liquid fluid that can carry at least a portion of the acoustic signal through the cross-section of the pipeline. In some implementations, a subsequent acoustic signal is transmitted across the cross-section of the pipeline.

At 210, a portion of the acoustic signal can be received at a time instant or at multiple time instants by an acoustic signal receiver, attached to a second location on the cross-section of the pipeline that is connected to an acoustic signal evaluator. The received acoustic signal includes an amplitude determined based on a deviation in pressure from a mean ambient pressure. At 212, a quantity of the gaseous fluid and a quantity of the liquid fluid passing the cross-section of the pipeline can be determined at a time instant. In some implementations, the quantity of the gaseous fluid and the quantity of the liquid fluid passing the cross-section of the pipeline can be determined by a computing system (e.g., the computing system 102 in FIG. 1A). The quantity of the gaseous fluid and the quantity of the liquid fluid can be determined based, in part, on an energy of the portion of the acoustic signal carried through the cross-section and an energy of the transmitted acoustic signal. The quantity of the gaseous fluid and the quantity of the liquid fluid passing the cross-section of the pipeline based, can be determined in part by determining that the energy of the portion of the acoustic signal carried through the cross-section and the energy of the transmitted acoustic signal are substantially equal and by determining that multiphase fluid includes more liquid fluid than gaseous fluid. The energy of a continuous-time acoustic signal x(t) can be defined as:

$$E_S = (x(t), x(t)) = \int_{-\infty}^{\infty} |x(t)|^2 dt$$

The energy of an acoustic signal can be determined using a PC/DSP (e.g., the computing system 102 in FIG. 1A) that can process the following equation:

$$E_S = \sum_{n=1}^{N} |x_n|^2 \Delta t$$

wherein, $E_s$ is the energy of the portion of the acoustic signal carried through the cross-section, $\Delta t$ is a sampling interval, and $x_n$ is voltage and n is a sample number. The measurement takes place starting at a time t=0 with a sampling interval of $\Delta t$ including a total of N measurements and the voltage can be expressed as:

$$x_n = x(n \cdot \Delta t), 1 \leq n \leq N$$

The energy can be computed for every 1000 cycles of the received acoustic signal. For a system (transmitter and receiver) operating in the range of 0.5-2 MHz at a central frequency of 1 MHz, the energy can be computed for every 1000 cycles, which is equal to 1000 energy measurements per second. Every fifty measurements can be averaged together, which results in twenty averaged measurements per second. In some implementations, a user interacting with the computing system through a GUI can select the averaging parameters.

At 214, a composition of the multiphase fluid flowing through the cross-section during the time instant and the plurality of subsequent time instants can be determined at a time instant. In some implementations, the composition of the multiphase fluid can be determined by a computing system (e.g., the computing system 102 in FIG. 1A). For example, in a two-phase flow, an approximate measurement of liquid hold up can also be determined from the energy of the received acoustic signal. The energy of the received acoustic signal can be stored as a time series of data points $E_S$. It is possible to perform a Fourier Transform over a sufficiently long measurement window greater than the period of the slugs. The Fourier Transform can convert the time series of energy measurements $E_S$ into a frequency spectrum of data points in units of energy per root Hertz and it can be defined as $E_{Sm}$. The index m represents a measurement taking place every 0.001 s using the parameters above. The characteristic frequencies of the slug flow can manifest as one or more frequency peaks within the frequency spectrum generated by the Fourier Transform. Such peaks can be detected either through simple thresholding or through more complex peak fitting algorithms such as Gaussian peak finding algorithms.

Successive spectra can be obtained either through continuous acquisition of a moving sampling window, or through successive acquisitions of energy data. The evolution of the slugging frequency spectrum can be monitored as a function of time. Peak tracking algorithms can be used to monitor the evolution of the slug flow as a function of time. An acoustic signal that passed through a liquid without gas has maximum acoustic energy, which can be equaled to a normalized value of one, corresponding to zero loss. The energy of the received acoustic signal for the 100% liquid case can be defined as:

$$E_{max} = \max(E_{Sm})$$

The energy of the received acoustic signal decreases with increased amount of gas. In case the entire region between the transmitter and the receiver is filled with gas, the energy of the received acoustic signal is reduced to zero and the loss is maximum (normalized to one). In any intermediate state, in which the fluid between the transmitter and the receiver includes a mixture of liquid and gas, the energy is between zero and one. The energy of the received acoustic signal for any intermediate state can be plotted over time and computed using the following relation:

$$E_{S,normalized} = \frac{E_{Sm}}{E_{max}}$$

The energy of the received acoustic signal and the loss can be used to determine the composition of the fluid in the wellbore, such as the gas volume fraction. To compute the value indicating the gas fraction, the quantity:

$$1 - E_{S,normalized}$$

is calculated. The normalized energy of the received acoustic signal can exhibit a monotonic dependency with respect to the gas fraction in the measurement. Through experimentation, the dependency can be calibrated to provide an estimate of the amount of gas in the flow.

The calculation of the composition of the fluid in the wellbore can also include the geometry of the wellbore. In some implementations, the computing system (e.g., the computing system 102 in FIG. 1A) can average the determined parameters over a longer period of time, such as 20-30 or more measurements, and consequently increase the accuracy of the energy measurement and determination of fluid composition. Process 200 can be included in training algorithms and optimization of flow control hardware, which can minimize flow. Process 200 can also be coupled with arrays of sensors so that precursor conditions to slugging could be detected and the slugging itself could be prevented.

Figure 3:
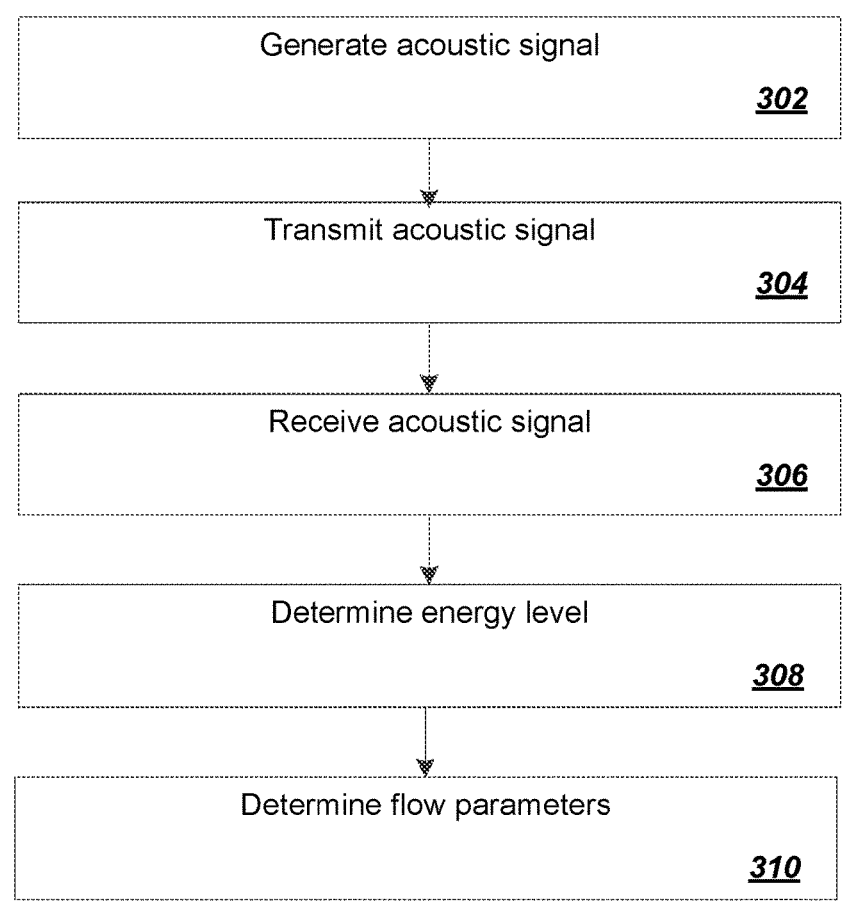
FIG. 3 is a flowchart of another example process for monitoring slug flow.

FIG. 3 is a flow chart showing an example process 300 for monitoring slug flow. At 302, an electric signal can be generated by a signal generator (e.g., signal generator 132 in FIG. 1B). At 304, the electric signal is converted into an acoustic signal and is transmitted across a cross-section of a pipeline, though which a multiphase fluid is flowing. The signal conversion and transmission of the acoustic signal across the cross-section of the pipeline can include transmitting the acoustic signal through an acoustic transmitter attached to an outer surface of the pipeline at a first location (as illustrated in FIG. 1A).

At 306, the acoustic signal is received by an acoustic receiver. The reception of the acoustic signal carried by the multiphase fluid through the cross-section of the pipeline can include receiving the acoustic signal carried by the multiphase fluid at an acoustic receiver attached to an outer surface of the pipeline at a second location that is diametrically opposite on the cross-section from the first location. At 308, the energy level of the received acoustic signal is determined by a computing system (e.g., the computing system 102 in FIG. 1A). At 310 the flow parameters in the wellbore are determined by the computing system (e.g., the computing system 102 in FIG. 1A). The flow parameters can include the include frequency, velocity and length of the slugs.

In some implementations, the flow parameters can be determined based on the length of liquid slug body LS and length of elongated bubble LB. The length of liquid slug body LS and length of elongated bubble LB can be calculated from a time-energy plot. The total length of a cell is considered as being: LS+LB. The frequency of the slug can be calculated using the formula 1/(LS+LB). For a system configuration including at least two acoustic transmitter-receiver pairs (as illustrated in FIG. 1A), which are located at a distance of d from each other, the velocity of slug flow can be calculated by correlating the acoustic signal received by two pairs and calculating the time it takes for a slug to travel from one acoustic pair to other (Δt). The slug velocity can be calculated using the formula v=d/Δt. In some implementations, a similar correlation method can be applied to compute the slug velocity using a linear array transducer that receives a separate signal at the first and last element. In some implementations, the determined flow parameters can also include relative density ratio of one fluid to the other, difference in viscosity between fluids and velocity (slip) of each fluid.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus.

What is claimed is:

1. A method comprising:
at a time instant, transmitting an acoustic signal across a cross-section of a pipeline flowing multiphase fluid comprising gaseous fluid and liquid fluid, wherein a portion of the acoustic signal is carried through the cross-section of the pipeline by the multiphase fluid, wherein, before transmitting the acoustic signal, a strength of the acoustic signal is increased to compensate for attenuation of the acoustic signal across the cross-section of the pipeline; and
determining, at the time instant, a first quantity of the gaseous fluid and a second quantity of the liquid fluid passing the cross-section of the pipeline based, in part, on an energy of the portion of the acoustic signal carried through the cross-section of the pipeline and at least a portion of a total energy of the transmitted acoustic signal by determining the energy of the portion of the acoustic signal carried through the cross-section of the pipeline, wherein the energy of the portion of the acoustic signal carried through the cross section is determined using the following equation: $E_S = \sum_{n=1}^{N} |x_n|^2 \Delta t$, wherein $E_s$ is the energy of the portion of the acoustic signal carried through the cross section, $\Delta t$ is a sampling interval, $x_n$ is voltage and n is sample number.

2. The method of claim 1, further comprising:
at each subsequent time instant of a plurality of subsequent time instants:
transmitting a subsequent acoustic signal across the cross-section of the pipeline, wherein a portion of the subsequent acoustic signal is carried through the cross-section of the pipeline by the multiphase fluid, and
determining, at the subsequent time instant, a third quantity of the gaseous fluid and a fourth quantity of the liquid fluid passing the cross-section of the pipeline based, in part, on an energy of the portion of the subsequent acoustic signal carried through the cross-section of the pipeline and an energy of the transmitted subsequent acoustic signal; and
determining a composition of the multiphase fluid flowed through the cross-section of the pipeline during the time instant and the plurality of subsequent time instants.

3. The method of claim 1, wherein transmitting the acoustic signal across the cross-section of the pipeline comprises:
attaching an acoustic signal transmitter to a first location on the cross-section of the pipeline; and
connecting an acoustic signal generator to the acoustic signal transmitter, the acoustic signal generator to generate the acoustic signal.

4. The method of claim 3, wherein the acoustic signal transmitter is attached to transmit the acoustic signal at a beam angle ranging between about 5° and 15°.

5. The method of claim 3, wherein the acoustic signal transmitter is configured to generate an acoustic signal in a frequency range of between about 0.5 MHz and 2.0 MHz.

6. The method of claim 3, wherein the acoustic signal generator is configured to generate and transmit an electric signal to the acoustic signal transmitter, and wherein the acoustic signal transmitter is configured to convert the electric signal into the acoustic signal.

7. The method of claim 6, wherein the electric signal is amplified before converting the electric signal into the acoustic signal.

8. The method of claim 3, further comprising
attaching an acoustic signal receiver to a second location on the cross-section of the pipeline; and
connecting an acoustic signal evaluator to the acoustic signal receiver.

9. The method of claim 8, wherein the acoustic signal transmitter and the acoustic signal receiver are attached at diametrically opposite ends of the cross-section of the pipeline.

10. The method of claim 1, wherein determining, at the time instant, the quantity of the gaseous fluid and the quantity of the liquid fluid passing the cross-section of the pipeline based, in part, on an energy of the portion of the acoustic signal carried through the cross-section and an energy of the transmitted acoustic signal comprises:
determining that the energy of the portion of the acoustic signal carried through the cross-section and the energy of the transmitted acoustic signal are substantially equal; and
determining that multiphase fluid comprises more liquid fluid than gaseous fluid.

11. The method of claim 1, wherein determining, at the time instant, a quantity of the gaseous fluid and a quantity of the liquid fluid passing the cross-section of the pipeline based, in part, on an energy of the portion of the acoustic signal carried through the cross-section and an energy of the transmitted acoustic signal comprises:
   determining that the energy of the portion of the acoustic signal carried through the cross-section is substantially less than the energy of the transmitted acoustic signal; and
   determining that multiphase fluid comprises substantially more gaseous fluid than liquid fluid.

* * * * *